United States Patent [19]

Kirkup et al.

[11] Patent Number: 4,876,365
[45] Date of Patent: Oct. 24, 1989

[54] INTERMEDIATE COMPOUNDS FOR PREPARING PENEMS AND CARBAPENEMS

[75] Inventors: Michael P. Kirkup, Somerset; Stuart W. McCombie, Caldwell, both of N.J.

[73] Assignee: Schering Corporation, Kenilworth, N.J.

[21] Appl. No.: 279,751

[22] Filed: Dec. 5, 1988

[51] Int. Cl.[4] .......................................... C07D 303/02
[52] U.S. Cl. .................................. 549/215; 540/200; 549/214
[58] Field of Search ................. 549/214, 215; 540/200

[56] References Cited

U.S. PATENT DOCUMENTS

| | | | |
|---|---|---|---|
| 4,301,074 | 11/1981 | Christensen et al. | 260/245.2 R |
| 4,378,314 | 3/1983 | Menard et al. | 260/239 A |
| 4,383,945 | 5/1983 | Hashimoto et al. | 260/239 A |
| 4,388,310 | 6/1983 | Christensen et al. | 424/200 |
| 4,504,485 | 3/1985 | McCombie et al. | 514/192 |
| 4,517,124 | 5/1985 | Broom | 260/245.2 R |
| 4,530,793 | 7/1985 | Girijavallabhan et al. | 260/245.2 R |
| 4,584,133 | 4/1986 | Girijavallabhan et al. | 245.2 R/ |
| 4,614,614 | 9/1986 | Ernest et al. | 540/359 |
| 4,623,643 | 11/1986 | Alpegiani et al. | 514/196 |
| 4,663,451 | 5/1987 | Hanessian et al. | 540/304 |
| 4,675,317 | 6/1987 | DiNinno et al. | 514/192 |
| 4,740,595 | 4/1988 | Chackalamannil | 540/200 |

FOREIGN PATENT DOCUMENTS

| | | |
|---|---|---|
| 0013662 | 1/1980 | European Pat. Off. |
| 0078026 | 10/1982 | European Pat. Off. |
| 0126587 | 5/1984 | European Pat. Off. |
| 0181831 | 5/1986 | European Pat. Off. |
| 2013674 | 8/1979 | United Kingdom. |
| 2144419 | 3/1985 | United Kingdom. |
| 2156814 | 10/1986 | United Kingdom. |

OTHER PUBLICATIONS

J. Am. Chem. Soc. vol. 107, 1985, pp. 1438–1439.
"A New Synthetic Strategy for the Penems, Total Synthesis of (5R,6S,8R)-6-(a-Hydroxyethyl)-2-(hydroxymethyl)penem-3-Carboxylic Acid", Am. Chem. Soc. 1985, 107, 1438–1439. Stephen Hanessian, Agnelo Bedeschi, Carlo Battistine & Nicola Mongelli.
"Oxidative N-Dearylation of 2-Azetidinones, p-Anisidine as a Source of Azetidinone Nitrogen", David R. Kronenthal, C. Y. Han, & Martha K. Taylor, J. Org. Chem. 1982, 47, 2765–2768.
Efficient Preparation of 6,6-Dihalopenicillanic Acids, Synthesis of Penicillanic Acid S,S-Dioxide (Sulbactam), R. A. Volkmann, R. D. Carroll, R. B. Drolet, M. L. Elliott, & B. S. Moore, J. Org. Chem. 1982, 47,3344–3345.
"New Short Step Synthesis of 3-Hydroxyethyl-4-Cyanoazettidin-2-One Derivative: A Potential Percursor of the Penems and the Carbapenems", Masao Shiozaki, Hiroshi Maruyama & Noboru Ishida, Heterocycles, vol. 22, No. 8, 1984 pp. 1725–1726.
"Stereocontrolled Synthese of Chiral Intermediates of Thienamycin From Threonines", Masao Shiozaki, Noboru Ishida, Tetsuo Hiraoka, and Hiroaki Yanagisawa, Tetrahedron Letters, vol. 22, No. 51, pp. 5205–5208, 1981.
"Stereospecific Synthesis of Chiral Precursors of Thienamycin From L-Threonine", Masao Shiozaki, Noboru Ishida, Tetsuo Hiraoka & Hiroshi Maruyama, Tetrahedron vol. 40, No. 10, pp. 1795 to 1802, 1984.
"Synthesis of Optically Active Azetidin-2-Ones From L-Threonine"-Hiroaki Yanagisawa, Akiko Ando, Masao Shiozaki & Tetsuo Hiraoka, Tetrahedron Letters-vol. 24, No. 10, pp. 1037–1040, 1983.
"The Chemistry of Penicillanic Acids, Part I; 6,6-Dibromo- and 6,6-Diiodo-derivatives", J. P. Clayton, Chemistry Dept., Beecham Research Lab., Brockham Park, Betchworth, Surrey, J. Chem. Soc. (C), 1969. pp. 2123–2127.
"An Efficient Synthesis of 2-Substituted-Thio-6-Hydroxyethyl-Penem-3-Carboxylic Acids via 2-Thioxopenams",—W. J. Leanza, Frank DiNinno, David A. Muthard, R. R. Wilkerning, Kenneth J. Wildonger, R. W. Ratcliffe & B. G. Christensen, Tetrahedron vol. 39, No. 15, pp. 2505 to 2513, 1983.
Synthese Silylierter 2-Amino-3-hydroxycarbonsaure-derivative, T. Oesterle and G. Simchen, Synthesis, vol. 4, 403–6, Apr. 1985.
Ring Transformations in Reactions of Heterocyclic Halogano Compounds with Nucleophiles, H. Van Meeteren and H. Van der Plas, Recl. Trav. Chim. Pays—Bas; 90(2), 105–16 (1971).
Activatim of Carbonyl Groups by Diphenyl 2-oxo-3-oxazolinyl Phosphonate, T. Kunieda, T. Higuchi, Y. Abe, M. Hirobe, Tetrahedron 39(20), 3253–60 (1983).
"Nuclear Analogues of β-Lactam Antibiotics, 2, The Total Synthesis of 8-Oxo-4thia-1-azabicyclo[4.2.0]oct-2-ene-2-carboxylic Acids[1]", D. Boles Bryan, Ralph F. Hall, Kenneth G. Holden, William F. Huffman, John G. Gleason, Journal of the American Chemical Society, /99:7/Mar. 30, 1977, pp. 2353–2355.
"Stereospecific Synthesis of D-Isothreonin From 1-Threonine"—Yasuyuki Shimohigashi, Michinori Waki, and Nobuo Izumiya, Bulletin of the Chemical Society of Japan, vol. 52 (3), 949–950 (1979).
Synthesis of Methyl 2-(Methyltrifluoroacetylamino)-3-(trimethylsiloxy)-alkanoates and N-Methyl-N-trifluoroacetyldidehydroamino Acid Methyl Esters, G. Simchen, D. Schultz and T. Seethaler, Synthesis, vol. 2, 127–9 (1988).
Specific Enolates from Alpha-Aminoketones, M. Garst, J. Bonfiglio, D. Grudoski and J. Marks, Tetrahedron Letters, (30)2671–4, (1978).
Specific Enolates from Alpha-Amino Ketones, M. Garst, J. Bonfiglio, D. Grudoski and J. Marks, J. Org. Chem., 45,2307–2315 (1980).

*Primary Examiner*—Glennon H. Hollrah
*Assistant Examiner*—Ba K. Trinh
*Attorney, Agent, or Firm*—Joseph T. Majka; Gerald S. Rosen

[57] ABSTRACT

Novel and useful silylenol intermediates for preparing penem and carbapenem antibacterials and a process for making selected intermediates are disclosed.

9 Claims, No Drawings

INTERMEDIATE COMPOUNDS FOR PREPARING PENEMS AND CARBAPENEMS

FIELD OF THE INVENTION

The present invention relates to novel intermediates or intermediate compounds useful for preparing penems and carbapenems, as well as methods for preparation of such intermediates.

BACKGROUND OF THE INVENTION

Penems and carbapenems are antibacterials which are useful in animal and human therapy. These antibacterials are active against a broad range of pathogens, including gram positive bacteria such as S. aureas, Strep. pyogenes and B. subtilis and gram-negative bacteria such as E. coli, Pseudomonas, Proteus organii, Serratia and Klebsiella.

Numerous methods for preparing such antibacterials have been disclosed in U.S. Pat. Nos. 4,675,317; 4,663,451; 4,623,643; 4,614,614; 4,584,133; 4,530,793; 4,517,724; 4,504,485; 4,378,314 and recently in the article by S. Hanessian et al. JACS, 1985, 107, page 1438. This reference discloses a multi-step process for preparing penems, including converting L-threonine into an epoxy acid, then to the epoxamide, followed by treatment of the epoxamide with potassium carbonate in dimethylformamide which results in ring closure to give the azetidinone. It would be highly desirable to utilize intermediates which require fewer reaction steps than for those disclosed in the Hanessian et al. article, in order to simplify the preparation of penem and carbapenem antibacterials. It would also be desirable to utilize an intermediate which allows an easy and convenient insertion of blocking groups to prepae the penem and carbapenem antibacterials. It would also be desirable to provide a process for making such selected intermediates in good yields and which allows selective insertion of a wide variety of blocking groups at the nitrogen atom.

SUMMARY OF THE INVENTION

The present invention is directed to novel silylenol ether intermediate compounds represented by the formula:

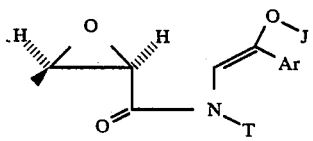

(III)

wherein
J is —SiR$^1$R$^2$R$^3$;
R$^1$, R$^2$ and R$^3$ independently represent lower alkyl or phenyl,
T is hydrogen, or a blocking group T', wherein T' is —CH$_2$OR$^4$ (wherein R$^4$ is lower alkyl or phenyl), 2-alkenyl, phenyl, phenylalkyl, or phenyl substituted with lower alkyl, alkoxy or halogen; and
Ar is phenyl or phenyl substituted with nitro (—NO$_2$), lower alkyl, alkoxy, or halo.

Preferably J is —Si(CH$_3$)$_2$C(CH$_3$)$_3$, Ar is phenyl, and T is H, —CH$_2$OCH$_3$ or —CH$_2$CH=CH$_2$.

The present invention is also directed to a process for preparing a compound of formula (III'')

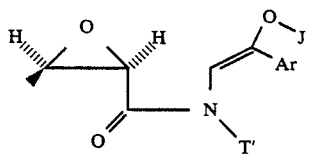

(III'')

wherein T' is a blocking group and J and Ar are as defined for compound (III). The process comprises contacting a compound of the formula:

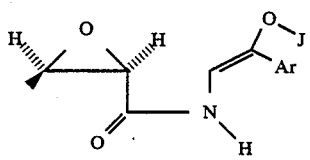

(III')

with a compound of the formula

XT'  (IV)

wherein J, Ar and T' are as defined hereinbefore for compound (III) and X is bromo, iodo, chloro, trifluoromethylsulfonyl (triflate) or para-toluene sulfonyl (tosyl), in the presence of a strong base and a solvent.

Preferably XT' of formula IV is allyl halide, more preferably allyl iodide. Also preferred is that the strong base is sodium hydride.

The intermediates of the present invention have the advantage of requiring fewer reaction steps in order to prepare the desired penem and carbapenem antibacterials then by the process described in the Hanessian et al. article. Thus, such intermediates can be used to simplify methods of preparing these antibacterials. When T in the compounds of formula (III) is hydrogen, this intermediate has the particular advantage of allowing easy insertion of a blocking group. The claimed process has the advantage of making selected intermediates wherein T' is a blocking group as defined hereinbfore, in good yields and with a high selectivity for insertion of a wide variety of blocking groups at the nitrogen atom.

DETAILED DESCRIPTION OF THE INVENTION

When utilized in the present specification and in the appended claims the terms listed hereinbelow, unless otherwise indicated are defined as follows:

"loweralkyl"—a straight or branched saturated hydrocarbon moiety (i.e. hydrocarbons having carbon-carbon single bonds) containing from one to six carbon atoms, such as for example, methyl, ethyl, propyl, isopropyl, butyl, isobutyl, tert-butyl, n-pentyl, n-hexyl and the like.

"◢"—donates a stereoisomeric configuration for methyl (—CH$_3$).

"alkoxy"—an alkyl moiety covalently bonded to an adjacent structural element through an oxygen atom, such as for example, methoxy (—OCH$_3$), ethoxy, propoxy, isopropoxy, butoxy, pentoxy, hexoxy and the like.

"phenylalkyl"—a phenyl moiety covalently bonded to an alkyl moiety of one to six carbon atoms such as, for example, phenylmethyl, 2-phenylethyl and the like.

"halogen" and "halo"—fluoro, chloro, bromo and iodo.

"2-alkenyl"—a straight or branched hydrocarbon moiety of three to sixteen carbon atoms having one carbon-carbon double bond on the second carbon atom such as 2-propenyl, 2-butenyl, 2-hexenyl, 4-methyl-2-hexenyl, 2-deceyl, 2-pentadecyl and the like.

"phenyl substituted"—the subsituents on the phenyl ring can number from one to five, and each substituent can be the same or different.

METHOD OF PREPARATION

Processes for preparing the intermediates of the present invention can be illustrated as follows:

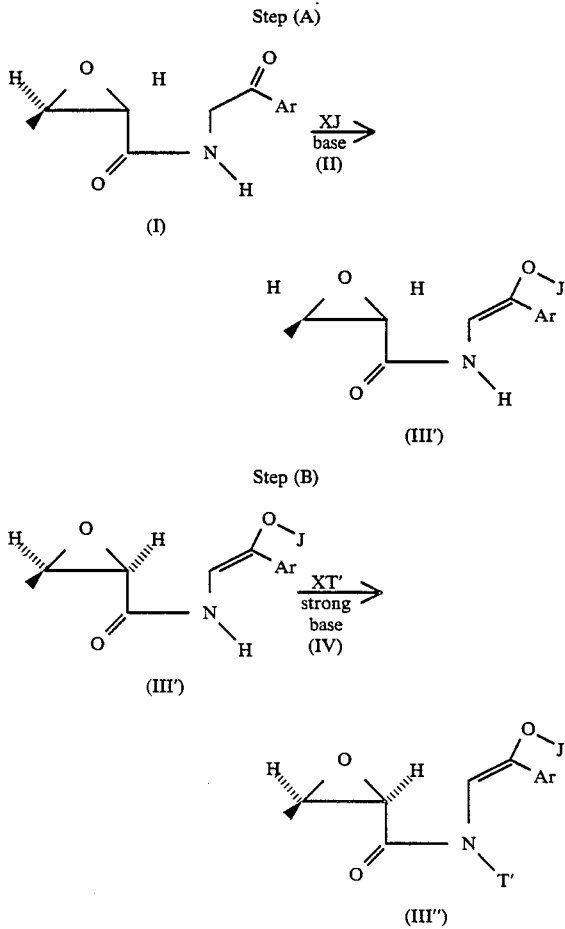

In Step (A) the silylenol ether compound of formula (III') (i.e. T is hydrogen) can be prepared by contacting a phenacyl glycidamine of formula (I) with silyl compound, XJ, of formula (II)

wherein J is as defined hereinbefore, and

X is a suitable leaving group, such as, but not limited to bromo, iodo, triflate or tosyl; in the presence of a solvent in amounts and under conditions effective to form the silylenol ether (III').

The phenacyl glycidamide (I) can be contacted with the silyl compound (II) at temperatures ranging from about zero degrees Centigrade (0° C.) to about ambient in the presence of a base, preferably 1,8-diazabicyclo[5.4.0]undec-7-ene (DBU). The reactants can be contacted at ambient pressures although pressures less than or greater than ambient can be employed. The reactants are contacted for a time effective to complete the reaction, typically for a period ranging from about 5 minutes to about 24 hours or more. The contacting can be conducted in the presence of solvents such as the chlorinated hydrocarbons including carbon tetrachloride ($CCl_4$), preferably methylene chloride ($CH_2Cl_2$) and dichloroethane; aliphatic hydrocarbons such as C-1 to C-20 alkanes, cyclic or acyclic; aromatic hydrocarbons such as benzene, toluene, xylene, alkylbenzenes and the like; ethers such as diethyl ether and tetrahydrofuran (THF) or mixtures thereof.

After the reaction is completed, the desired silylenol ether of formula (III') can be recovered by conventional separatory and recovery methods such as chromatography, crystallization and the like. Alternatively, the silylenol ether (III') can be used in its crude form to prepare other silylenol ethers (III") having a blocking group (i.e. T') at the nitrogen atom.

In Step (B), other silylenol ethers (III") having a blocking group (i.e. T') at the nitrogen atom can be prepared by contacting compound (III') with XT' of formula (IV), wherein X and T' are as defined hereinbefore, and the contacting is performed in the presence of a strong base and a solvent under conditions effective to yield the desired silylenol ether (III"). Preferably XT' of formula (IV) is allyl halide, most preferably allyl iodide or chloromethylmethyl ether. Bases which can be employed in Step (B) are generally non-aqueous bases such as lithium diisopropyl amide, lithium bis(trimethylsilyl)amide, sodium bis(trimethylsilyl)amide and potassium bis(trimethylsilyl)amide; potassium t-butoxide or bases of alkali and alkaline earth metals including carbonates such as sodium, potassium and cesium carbonates; hydroxides such as sodium and potassium hydroxides; hydrides such as sodium or potassium hydrides; preferably the base is sodium hydride. Other strong bases which may be suitably employed are disclosed in "Modern Synthetic Reactions" by H. House, W. A. Benjamin, Inc., Menlo Park, Calif., 1972, 856 pages. The silylenol ether of formula (III') can be contacted with the strong base in an amount effective to remove the proton on the nitrogen atom, generally eqimolar amounts of base to silyenol ether (III'). Solvents which can be suitably employed in Step (B) include anhydrous polar aprotic solvents such as DMF, THF, and dimethoxyethane (DME), preferably DMF. The solvent can be employed in amounts effective to solubilize or homogenize the reactants in the reaction mixture, such as in amounts ranging from about 1 to about 5000 parts by weight of the silylenol ether (III'). The contacting is performed under conditions similar to those described for step (A). After the reaction is completed, the desired silylenol ethers (III") can be recovered by the methods described in Step (A).

Examples 1 to 3 which follow illustrate representative methods for preparing the compounds of the present inventoion, but as such, should not be construed as limitations upon the overall scope of the same.

EXAMPLE 1

1-t-BUTYLDIMETHYLSILYLOXY-2-(2R,3R)-β-METHYL GLYCIDAMIDOSTYRENE

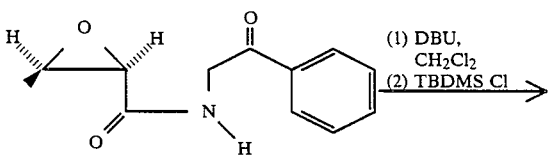

-continued

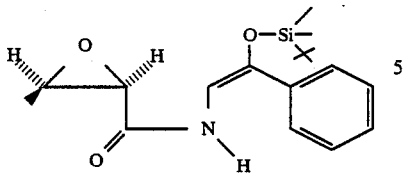

The epoxide, (2R,3R)-N-phenacyl-β-methyl glycidamide (5.05 grams (g)) is dissolved in 50 milliliters (ml) of methylene chloride and cooled to a temperature of 0° C. A solution of 1,8-diazabicyclo[5.4.0]undec-7-ene (4.94 g) in 10 ml of CH₂Cl₂ is added followed 5 minutes later by a solution of t-butyldimethylsilyl chloride (TBDMSCl) (4.0 g) in 3 ml of CH₂Cl₂. The mixture is stirred under nitrogen for 8 hours. Addition of 10 ml water followed by extraction into ether, drying the ether layer over magnesium sulfate (MgSO₄) and purification on silicagel with (CH₂Cl₂—5% acetone/CH₂Cl₂) affords 7.3 g (95 percent yield) of the title product, a silylenol ether. ¹H NMR(CDCl₃): δ0.1 (6H, S); 1.02 (9H, S); 1.36 (3H, d, J=6.2 Hz); 3.31 (1H, quartet, J=6.2 Hz); 3.58 (1H, d, J=6.1 Hz); 6.8 (1H, d, J=13 Hz); 7.21–7.45 (5H, M); 7.97 (1H, brd, J=13 Hz).

EXAMPLE 2

1-t-BUTYLDIMETHYLSILYLOXY-2-(N-METHOXYMETHYL)2R,3R)-β-METHYL-GLYCIDAMIDOSTYRENE

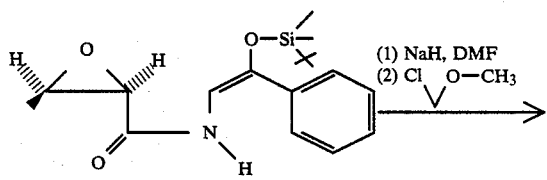

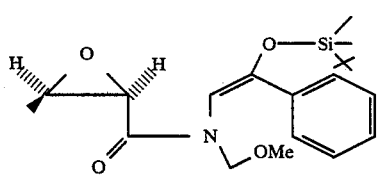

The silylenolether (1.0 g) of Example 1 is dissolved in 15 ml of dry dimethylformamide (DMF) and the stirred solution is cooled to 0° C. A suspension of 80 mg of sodium hydride (oil removed with hexane) in DMF is added via pipette over several minutes. After evolution of gas ceases (25 min) a solution of chloromethylmethylether (266 mg) in 5 ml of DMF is then added via syringe. The mixture is removed from the ice bath and allowed to stand under nitrogen for two hours. The mixture is diluted with 25 ml water and the product is extracted into ether, dried over magnesium sulfate (MgSO₄) and chromatographed on silica gel with (5% EtoAc/CH₂Cl₂ to 15% EtOAc (CH₂Cl₂) to afford 1.1 g (97 percent yield) of title product. ¹H NMR(CDCl₃): δ-0.04 (6H, S); 0.94 (9H, S), 1.37 (3H, J=6.1 Hz); 3.30 (1H, partially obscured quartet, J=6.1 Hz); 3.35 (3H, S); 3.84 (1H, d, J=6.1 Hz); 4.87 (1H, d, J=10.0 Hz 5.28 (1H, d, J=10.0 Hz); 5.98 (1H, S); 7.2–7.7 (5H, br.m).

EXAMPLE 3

1-t-BUTYLDIMETHYLSILYLOXY-2-(N-ALLYL)(2R,3R)-β-METHYL GLYCIDAMIDOSTYRENE

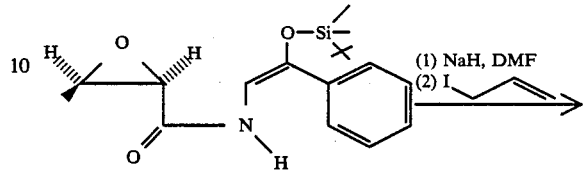

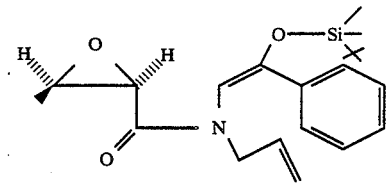

The silylenolether (1.0 g) of Example 1 is dissolved in DMF and to the cooled solution (0° C.) is added a suspension of 92 mg of sodium hydride (oil removed with hexane) over several minutes. After 45 minutes, a solution of allyliodide (560 mg) is added in 2 ml of DMF and allowed to stand at room temperature for one hour. Water is added (25 ml) and the product is extracted into ether. The ether layer is dried over MgSO₄ and concentrated to an oil. Chromatography on silica gel (CH₂Cl₂) gives 0.68 g (60.7 percent yield) of title product. ¹H NMR (CDCl₃): δ0.01 (6H, S); 1.25 (3H, d, J=6.3 Hz), 3.2 (1H, quartet, J=6.3 Hz); 3.7 (1H, d, J=6 Hz); 4.0 (1 Hz, dd, J=15.5, 7.5 Hz); 4.4 (1H, dd, J=15.5, 6.5 Hz); 4.9–5.3 (2H, m); 5.65 (1H, m); 5.77 (1H, S); 7.0–7.5 (5H, m).

Examples 4–7 which follow, illustrate representative methods of using the invention to prepare penems, but as such should not be construed a limitation upon the overall scope of the same.

EXAMPLE 4

N-METHOXYMETHYL-(3S,4S,5R)-3-(1-HYDROXYETHYL)-4-BENZOYLAZETIDINONE

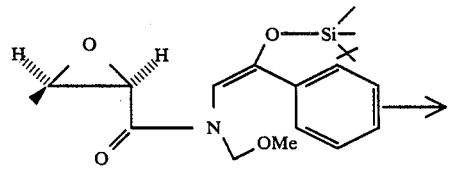

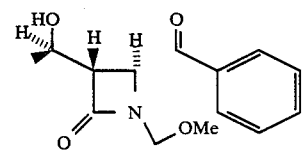

To a solution of dry benzyl trimethyl ammonium fluoride (40 mg) in dry benzene is added a solution of 100 mg of the silyl enolether of Example 2 in dry THF. The reaction is stirred under nitrogen for 45 min. and then the reaction is quenched with (20 ml) aqueous NaHCO₃. The organic material is extracted into ethylacetate, dried over MgSO₄ and purified on silica gel (10% EtoAC/CH₂Cl₂) yielding 54.2 mg (77 percent yield) mg of β-lactam. ¹H NMR (CDCl₃, azetidinone) for the β-lactam: δ1.25 (3H, d, J=6.1 Hz); 3.25 (1H, m); 3.38 (3H, S); 4.25 (1H, m); 4.32 (1H, d, J=14.5 Hz); 4.81 (1H, d, J=14.5 Hz); 5.2 (1H, d, J=3 Hz); 7.2-7.8 (3H, m); 8.0-8.25 (2H, m).

EXAMPLE 5
N-METHOXYMETHYL-N-PHENACYL(2R,3R)-β-METHYL GLYCIDAMIDE

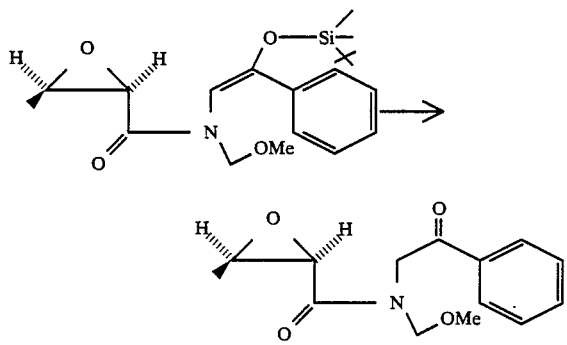

To a solution of the N-methoxymethyl silylenol ether (200 mg) of Example 2 in wet THF, is added 1.1 equivalents (40 mg) of sodium fluoride. A catalytic amount of tetrabutyl ammonium acetate is added and the reaction is complete after 45 min. Aqueous workup and extraction into ethylacetate followed by chromatography on silica gel (5% acetone/CH₂Cl₂) affords 210 mg (94 percent yield) of the title compound, ¹H NMR (CDCl₃): δ1.3 (3H, d, J=6.1 Hz); 3.25 (1H, multiplete, obscured); 3.33 (3H, s); 3.75 (1H, d, J=6.1 Hz); 4.75-5.1 (HH, m); 7.2-7.7 (3H, m), 7.8-8.1 (2H, m).

EXAMPLE 6
N-METHOXYMETHYL-(3S,4S,5R)-3-(1-HYDROXYETHYL)-4-BENZOYLAZETIDINONE

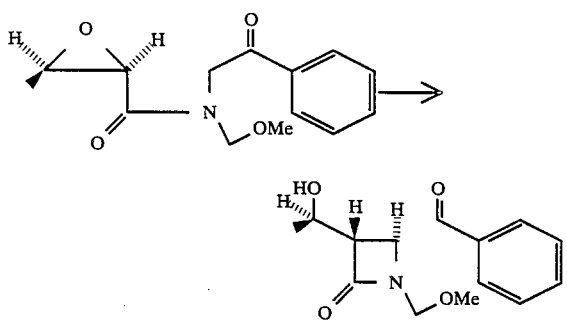

To a cold (8° C.) benzene solution of 301 mg of the epoxy amide (2R,3R) N-phenacyl-N-methoxymethyl-β-methyl glycidamide of Example 5 is added 1.5 ml of 1 molar (M) lithium bis(trimethylsilyl)amide in hexane kept at 8° C. for 1.5 hr. The reaction is quenched with dilute tartaric acid and the product is extracted into ethyl ether (Et₂O). Chromatography on silica gel (10 percent EtOAc/CH₂Cl₂) affords 225 mg of title product (75 percent yield). ¹H NMR (CDCl₃): δ1.25 (3H, d, J=6.1 Hz); 3.25 (1H, m); 3.38 (3H, S); 4.25 (1H, m); 4.32 (1H, d, J=14.5 Hz); 4.81 (1H, d, J=14.5 Hz); 5.2 (1H, d, J=3 Hz); 7.2-7.8 (3H, m); 8.0-8.25 (2H, m).

EXAMPLE 7
(2R,3R)-N-ALLYL-N-PHENACYL-β-METHYL GLYCIDAMIDE

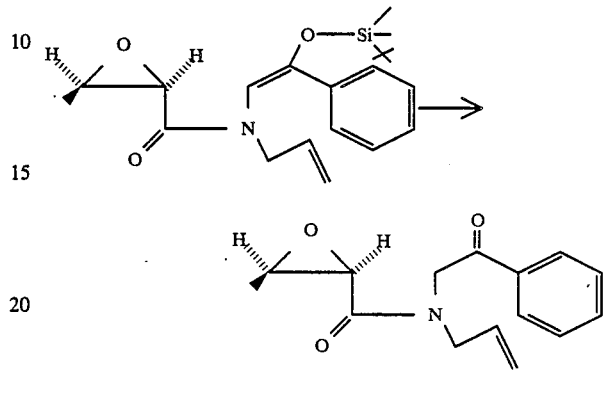

The N-allylsilylenolether (680 mg) of Example 3 is dissolved in aqueous THF (5 ml) and cooled to 0° C. A solution of tetrabutylammonium fluoride (570 mg) in THF (2 ml) is then added and the reaction is allowed to stand for 15 min. Water is added (10 ml) and the product is extracted into EtOAc driver over MgSO₄ and the concentrated residue is chromatographed on silica gel (10 percent EtOAc/CH₂Cl₂) to give 300 mg (64 percent yield) of title compound. ¹H NMR (CDCl₃): δ1.30 (3H, d, J=6 Hz); 3.1-3.6 (1H, m); 3.7 (1H, d, J=5 Hz); 4.15 (2H, dd, J=18.5, 6 Hz); 4.57 (1H, d, J=18.5 Hz); 5.0 (1H, d, J=18.5 Hz); 5.0-5.4 (2H, m); 5.5-6.0 (1H, m); 7.3-7.7 (3H, m); 8.0 (2H, dd, J=2, 7.5 Hz).

EXAMPLE 8
(3S,4S,5R)-N-ALLYL-3-(1-HYDROXYETHYL)-4-BENZOYLAZETIDINONE

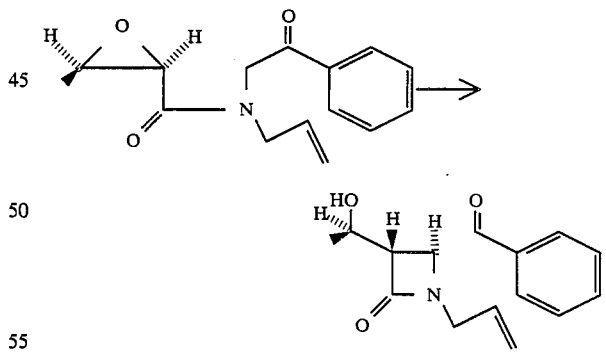

The purified epoxyamide (500 mg) of Example 7 is dissolved in 10 ml of anhydrous methylene chloride (CH₂Cl₂) and cooled to −20° C. A 1M solution of lithium bis(trimethylsilyl)amide in hexane (3.0 ml) is added via syringe. The mixture is allowed to stir under nitrogen for 3 hours. Then 500 mL of 5% tartaric acid (aqueous) is added and the product is extracted into CH₂Cl₂ (2×10 ml). The organic phase is washed with water (2×25 ml), dried over MgSO₄ and the solvent is evaporated under vacuum. Trituration with hexane/ether (1:2 ) (volume:volume) gives 364 mg (65 percent yield) of essentially pure title compound. (mp:

84°-86° C.): $^1$H NMR CDCl$_3$: 8.15 (dd, 2H, J=10, 2 Hz), 7.3-7.78 (m, 3H), 5.5-6.1 (m, 1H); 5.1-5.5 (m, 2H); 5.18 (d, 1H, J=2.5 Hz); 4.26 (m, 1H); 4.25 (ddd, 1H, J=19, 6, 2 Hz); 3.75 (dd, 1H, J=19, 7 Hz); 3.15 (dd, 1H, J=8, 2 Hz); 2.0 (br.d, 1H, J=7 Hz); 1.3 (d, 3H, J=7 Hz).

PREPARATION OF STARTING MATERIALS

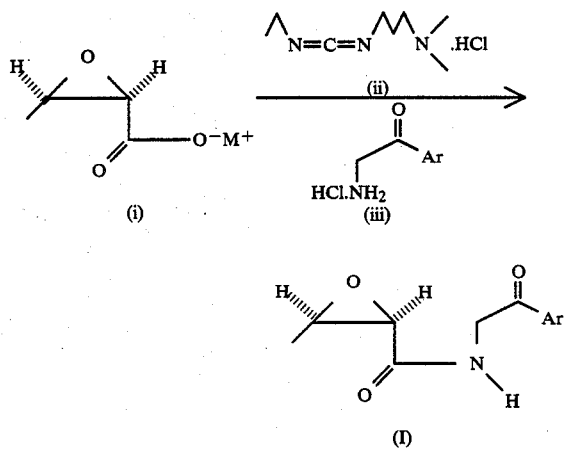

The phenyl epoxy amide (I), starting material can be prepared by contacting a glycidic acid salt (i) wherein M$^+$ is a alkali metal cation such as sodium or potassium, with phenylacyl amine hydrochloride (ii) and a carbodiimide acid coupling agent (iii) in a solvent such as tetrahydrofuran (THF) at temperatures of about 0° C. to about ambient to yield the compound of formula (I). The reactants can be contacted at ambient pressures, with stirring, for a time effective to substantially complete the reaction, a period ranging from about 5 minutes to about 24 hours or more. After the reaction is completed, the starting material of formula (I) can be recovered by conventional procedures such as those described hereinbefore.

The example which follows illustrates a representative method for preparing the starting materials used to prepare the intermediate compounds of the present invention but, as such, should not be construed as limitations upon the overall scope of the same.

EXAMPLE 9

(2R,3R)-N-PHENACYL-β-METHYL GLYCIDAMIDE

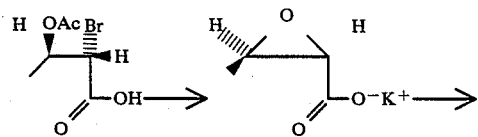

-continued

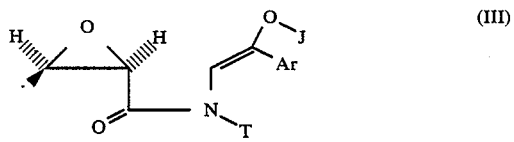

To a cold (0° C.) soluton of 1.4 grams (g) of potassium hydroxide (KOH) in 30 milliliters (ml) ethanol 2.25 g of (2S,3R)-2-bromo-3-hydroxy butyric acid derived from L-threonine is added and kept at room temperature for 30 minutes (min). The ethanol is then removed by vacuum distillation with gentle warming. The solid residue is pulverized and suspended in 50 ml dry tetrahydrofuran (THF), cooled to 10° C. and then 2.4 g 1-ethyl-3(3-dimethylaminopropyl)carbodiimide hydrochloride is added with rapid stirring followed by 2.06 g of phenacylamine hydrochloride. The mixture is stirred at room temperature for 1.5 hours (hr). Water (100 ml) is added and the product is extracted in to ethylacetate. Chromatography on silica gel (5% acetone/CH$_2$Cl$_2$) gives 1.76 g of the title product. $^1$H NMR (CDCl$_3$: δ1.4 (3H, d, J=7 Hz); 3.30 (1H, quartet, J=6.5 Hz); 3.55 (1H, d, J=6.5 Hz); 4.7 (1H, dd, J=14,5); 4.94 (1H, dd, J=14, 6.2 Hz); 7.2 (1H, br); 7.55 (1H, m); 8.0 (2H, brd, J=8 HZ).

While the present invention has been described in conjunction with the specific embodiments set forth above, many alternatives, modifications, and variations thereof will be apparent to those of ordinary skill in the art. All such alternatives, modifications and variations are intended to fall within the spirit and scope of the present invention.

We claim:

1. A compound represented by the formula

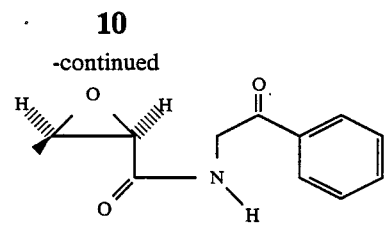

(III)

wherein
J is —SiR$^1$R$^2$R$^3$;
R$^1$, R$^2$ and R$^3$ independently represent lower alkyl or phenyl;
T is hydrogen, or a blocking group T', which is —CH$_2$OR$^4$ (wherein R$^4$ is alkyl or phenyl), 2-alkenyl, phenyl, phenylalkyl, or phenyl substituted with alkyl, alkoxy or halogen; and
Ar is phenyl or phenyl substituted with nitro, alkyl, alkoxy, or halo.

2. The compound of claim 1 wherein R$^1$, R$^2$ and R$^3$ each independently represents alkyl.

3. The compound of claim 1 wherein J is —Si(CH$_3$)$_2$C(CH$_3$)$_3$.

4. The compound of claim 1 wherein Ar is phenyl.

5. The compound of claim 1 wherein J is —Si(CH$_3$)$_2$C(CH$_3$)$_3$ and Ar is phenyl.

6. The compound of claim 1 wherein T is hydrogen.

7. The compound of claim 1 wherein T is —CH$_2$OCH$_3$ or —CH$_2$CH=CH$_2$.

8. The compound of claim 5 wherein T is hydrogen.

9. The compound of claim 5 wherein T is —CH$_2$OCH$_3$ or —CH$_2$CH$_2$=CH$_2$.

* * * * *